United States Patent [19]

Adler

[11] Patent Number: 4,541,803

[45] Date of Patent: Sep. 17, 1985

[54] METHOD AND APPARATUS FOR MEDIATING INTER-JAW BITING PRESSURE

[76] Inventor: Harold A. Adler, 1457 Eastwind Cir., Westlake Village, Calif. 91361

[21] Appl. No.: 519,413

[22] Filed: Aug. 1, 1983

[51] Int. Cl.⁴ .............................................. A61C 3/00
[52] U.S. Cl. ...................................... 433/141; 433/71
[58] Field of Search ................. 433/71, 150, 218, 141, 433/215

[56] References Cited

U.S. PATENT DOCUMENTS

| | | | |
|---|---|---|---|
| 2,183,624 | 12/1939 | Schwartz | 433/71 |
| 3,903,606 | 9/1975 | Oliver | 433/161 |
| 3,959,881 | 6/1976 | Kokal, Jr. | 433/70 |
| 4,219,619 | 8/1980 | Zarow | 433/218 |

*Primary Examiner*—Robert Peshock

[57] ABSTRACT

Method and apparatus for obtaining and maintaining optimum performance of inter-jaw biting musculature for seating and cementing dental crowns and bridges, such method including utilizing the biting musculature only within the limits of relaxed muscle-fiber length, using said apparatus as physiologically-appropriate contact and pressure reference for sensory-motor innervation feed-back from muscles and dental structures to determine and control muscle performance and using said apparatus as means for controlling inter-jaw muscle-fiber length and for pressure mediation and delivery between the upper and lower dental arches. A wafer is used between the teeth of opposing arches to mediate and transfer pressure during seating and cementing of dental crowns. The wafer is of one piece construction, injection molded of specifically resilient synthetic polymer composition material. One end is flat on its broadest two sides, the remainder is a similar but thinner middle layer covered on each broad side with multiple small raised hemispheres regularly arranged to abut multiple others at the base with restricted small open flat areas remaining between hemispheres. Thickness of the wafer is designed to permit jaw muscle biting pressure activity only within the limits of relaxed jaw muscle length.

9 Claims, 11 Drawing Figures

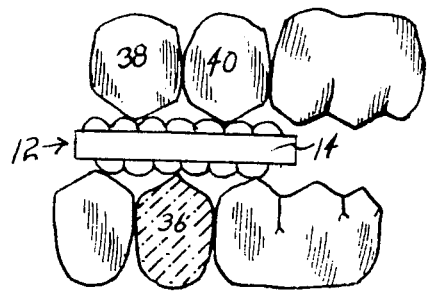
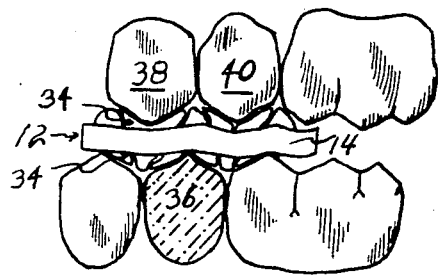
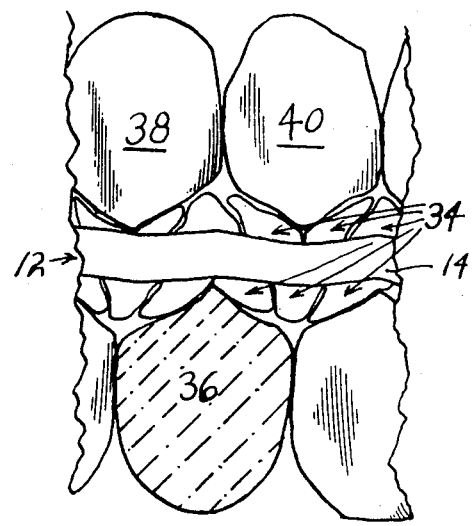
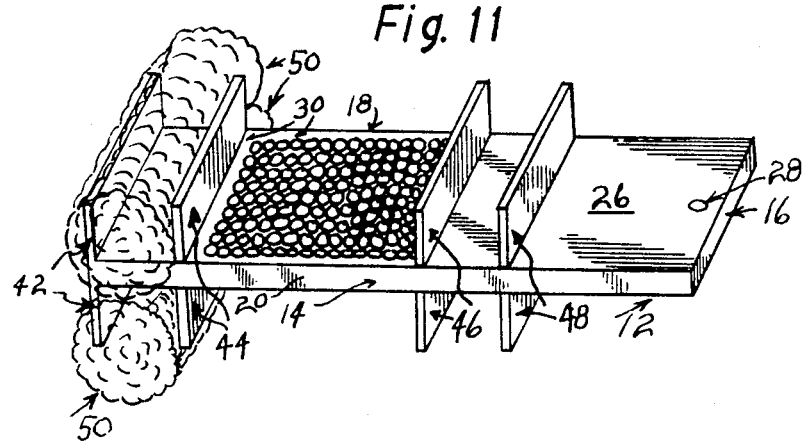

METHOD AND APPARATUS FOR MEDIATING INTER-JAW BITING PRESSURE

BACKGROUND OF THE INVENTION

This invention is directed to a method and means for optimizing muscular activity between the jaws as applied to a dental crown seating device for use during seating and cementing of dental crowns and bridges, which method and device mediates, maximizes, and transfers pressures transmitted through the teeth of opposing arches by the muscles of mastication as they contract to supply biting pressure utilized for the seating and cementing of dental crowns.

Whenever a dental patient requires placement of an artificial dental crown, or multiple crowns with artificial teeth interposed, known as bridges, such crowns and bridges must be cemented into position after manufacture. The crown or bridge is first placed over the tooth stump or stumps for which it was made and forced completely on to the stump under pressure, a process known as seating, to assure proper fit. For purposes of this application and clarity, the word "appliance" will be used to represent all of the various types of crowns and bridges, and will be used in the singular, although it should be understood that the crowns, artificial or natural, and the tooth stumps, may be singular or plural in the individual case. The trial-seated appliance is then removed from the stump, cleaned, dried, and internally coated with dental cement. It is then re-seated on the tooth stump. The patient is then required to bite forcefully against the seated appliance with sufficient pressure to hold it in position against the opposing hydraulic pressure of the cementing medium. This biting pressure should be maintained, without substantial change or movement of the jaws, for such period of time as is necessary for the dental cement used to undergo the chemical-mechanical change required for it to permanently harden and bond the appliance to the tooth stump. Prior art has dictated the use of wooden sticks, rolls of cotton, and various other devices to interpose between upper and lower teeth for the purpose of transmitting biting pressure from the muscles of mastication. While these prior art devices have been useful, they all have substantial problems in use. The major problem is that the jaw muscles tire rapidly, the patient is not able to maintain strong, steady biting pressure, and is forced to relax the muscles. The reason for this is that, as the muscles reach exhaustion, the patient experiences muscular discomfort. With growing discomfort, the patient discontinues biting pressure in order to ease the growing muscular discomfort and to rest. With the discontinuation of biting pressure, and relaxation of the muscles, the jaws also open to help further relax the muscles and ease discomfort. After thus relaxing and resting, the patient again closes the jaws and resumes firm biting pressure, only to quickly tire and relax again. Under these conditions, the appliance, and the internal layer of cement, is subjected to repeated periods of pressure and release of pressure. The appliance is seated against the stump each time by biting pressure. As the patient rests momentarily, pressure is released and the jaws separate. With the release of pressure and separation of the teeth, the internal hydraulic pressure of the viscous unhardened cement that now fills the space between the tapered tooth stump and the similarly tapered inner wall of the appliance, forces the appliance away from the tooth stump. Thus, the appliance is "pumped" up and down, repeatedly, each time the patient's jaw muscles tire and the consequent discomfort forces the patient to relax the muscle pressure to rest, even momentarily. This repeated movement of the appliance on and from the tooth stump interferes with normal hardening of the cement, prevents the cement from hardening uniformly, and increases the time required for cement hardening. These result in a weakened bond between tooth-stump and appliance, a poorer fit, and greatly shorten the useful life of the appliance. The health of the tooth stump is also threatened as the weakened cement is lost over time, and the resultant separation between tooth stump and appliance wall offers ideal conditions for hidden decay to occur. This invention recognizes a problem hitherto unrecognized or dealt with: that the rapid tiring of the jaw muscles that causes the previously referred to problems in seating and cementation is not just normal muscle tiring from exertion, but that this muscle-fiber exhaustion is brought about because the muscle-fibers are extended or stretched prior to and during contraction, and so are incapable of optimal performance. The same holds true if the fibers are compacted before and during use: pre-straining the muscle-fibers by stretching or compacting them, and maintaining that strain during muscular activity, greatly limits both the magnitude and duration of muscle perfpormance. It must be further recognized that the prior art has other problems associated with its use. Bite-sticks are frangible and too hard on initial contact, with negligible resilience. The delicate periodontal membrane between tooth root and bony socket is thus crushed repeatedly each time the patient bites down. In the same manner as biting on an unexpected bit of bone causes shock and distress to the tooth of the diner, biting against the hard stick shocks the teeth and periodontal ligament. However, because the teeth and their supporting tissues are usually anesthetized, the patient feels no pain, and even though damage is being done, neither patient nor dentist is aware of it at the time. Cotton rolls are extremely soft and very springy. As the patient bites against them, there is little or no resistance felt by the teeth. As the cotton is compacted by stronger biting pressure to where some resistance is noticeable, the compacted cotton remains springy, with continual variations of pressure and springiness over this range of compaction. This gives the patient a very poor and constantly varying pressure feedback reference against which to judge muscle effort in order to maintain the required steady, firm, and prolonged biting pressure required. Further, as very strong pressure is applied, the cotton compacts still more, to a thickness that brings about compaction of the muscle-fibers, stressing these fibers still more during their exertion, to the detrimental effects mentioned previously. What is more, as the cotton becomes wet with saliva, it compresses even more, compounding this effect. Other prior art devices have these same defects, singly or multiple, depending on their construction. These have been hitherto unrecognized problems of the prior art which individually and collectively prevent the dental patient from providing the steady, sustained, firm biting pressure required to provide proper conditions for seating and cementation of dental appliances. What is needed is a method and means for maximizing inter-jaw muscle activity, in duration and magnitude, to that required for seating and cementing dental appliances, and for the effective transfer and maintenance of such developed pressure under physiologically benign conditions to the tooth stump, cement and appliance.

SUMMARY OF THE INVENTION

In order to aid in the understanding of this invention, it can be stated in essentially summary form that it is a method and apparatus for obtaining and maintaining optimum performance of inter-jaw biting musculature for seating and cementing dental appliances, which method includes utilizing the biting musculature only within the limits of relaxed muscle-fiber length, effectively utilizing the feed-back sensory apparatus of the muscles and dental structures to determine and control muscle performance, and using the apparatus as means for controlling working inter-jaw muscle-fiber length within the desired limits of relaxed muscle-fiber length, and for physiologically appropriate pressure mediation and efficient transfer between the upper and lower dental arches. For purposes of convenience and this application, the apparatus is referred to as a wafer. The wafer is a thermoplastic synthetic polymer material in wafer form. The wafer serves to buffer the initial magnitude of bite force, and then acts as an efficient agent for transfer of bite force as pressure increases, while retaining minimum resilience necessary to avoid pressure shock to dental structures. Thickness of the wafer determines separation distance between the teeth of opposing jaws under biting pressure. Thickness and resilience of the wafer varies with the amount of biting pressure, but remains within the limits of jaw separation as determined by the resting position of the muscles of mastication. Muscle work which is initiated and carried on within the resting-length parameters of muscle-fiber is maximized, in both magnitude and duration, while strain is reduced to minimum. Wafer thickness is graded by composition and structure to respond to degree of biting force. Maximum thickness, greatest resilience, and poorest pressure transfer occur at weakest bite pressures, while minimum thickness, least resilience, and maximum pressure transfer occur at strong biting pressures. By additionally placing one or more wafers on the opposite side of the dental arch from the appliance being placed, the musculature of both sides of upper and lower jaws is utilized at the same pressure and muscle-length, and equal strain is thus carried by both lower jaw condyles (points of jaw rotation). Incorporated within the invention may be means to support rolls of cotton to assist dryness in the field of cementation, or other means to assist dental procedures.

Thus it is one object of this invention to provide a method for utilizing the inter-jaw musculature at optimum performance levels in both magnitude and duration, for the purpose of creating inter-jaw pressures to be utilized for seating and cementing dental appliances.

It is another object of this invention to provide a method for the efficient and physiologically-benign transfer of said inter-jaw pressures to dental appliances for their seating and cementation.

It is another object of this invention to provide a crown-seating wafer which is made of an injection-molded thermoplastic synthetic polymer material sufficiently hard at firm biting pressures to transmit pressure essentially unaltered and sufficiently resilient to avoid trauma to biological structures.

It is another object of this invention to provide a crown-seating wafer that provides a rapid, pressure-mediated, repeatable thickness and resilience gradient appropriate to the dental sensing apparatus as the jaws engage from minimum to maximum sustainable muscular pressure.

It is another object of this invention to provide a crown-seating device of such thickness and resilience as to gradually increase tooth-pressure-load as space decreases from the average maximum to minimum inter-jaw separation space provided by relaxed jaw musculature.

It is a further object of this invention to provide a crown-seating wafer of such thickness under strong, sustained biting pressure as to maintain separation space between the dental arches equivalent to the separation space between the arches that is present when the jaw muscles are at rest. al to maximum muscle contraction within relaxed muscle-fiber length.

It is a further object of this invention to provide a crown-seating wafer that will retain designed thickness and resilience under maximum sustainable pressure over a prolonged period.

It is another object of this invention to provide a crown-seating device which is also useful for retaining means for field-drying.

It is another object of this invention to provide an inexpensive, disposable, comfortable crown-seating device.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 8 is a front elevational view of the dental crown seating wafer placed between the side teeth of the upper and lower jaws before bite pressure is exerted.

FIG. 9 is a front elevational view of the dental crown seating wafer when strong biting pressure is exerted.

FIG. 10 is an enlarged detail of FIG. 9 showing the distortion and compaction of the hemispheres under biting pressure and the resilience and resistance of the solid core central layer.

FIG. 11 is an isometric view of an embodiment of the wafer with a means for supporting cotton rolls for field dryness.

DESCRIPTION OF THE PREFERRED EMBODIMENT

Figure 1:
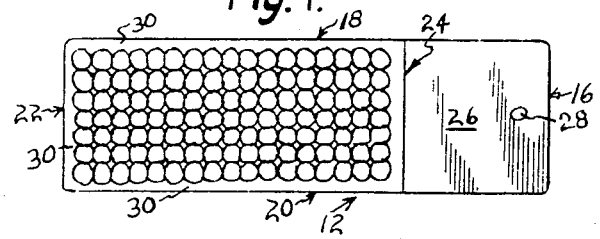
FIG. 1 is a top elevational view of the dental crown seating wafer of this invention.
Figure 2:
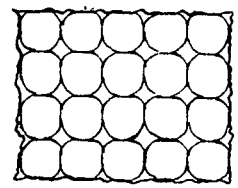
FIG. 2 is an enlarged detail of FIG. 1 showing the distribution and abutment of the hemispheres.
Figure 3:
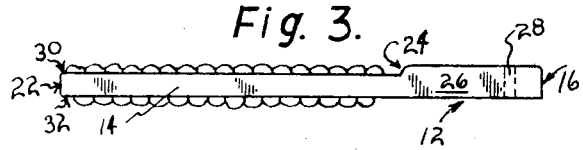
FIG. 3 is a side elevational view of the dental crown seating wafer.
Figure 4:
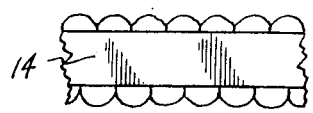
FIG. 4 is an enlarged detail of FIG. 3 showing hemisphere base abutment and difference of placement between upper and lower layers of hemispheres.
Figure 5:
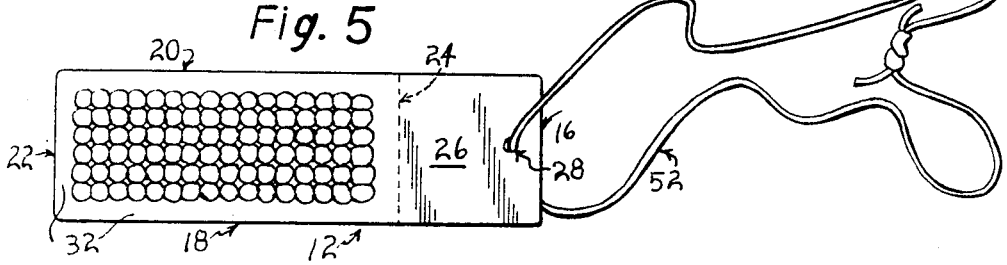
FIG. 5 is a bottom elevational view of the dental crown seating wafer.
Figure 6:
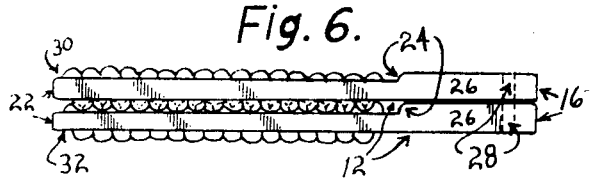
FIG. 6 is a side elevational view of two dental crown seating wafers placed together, one on top of the other.
Figure 7:
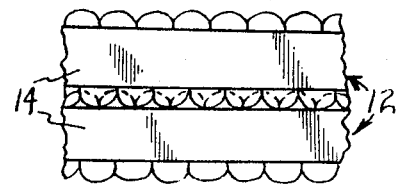
FIG. 7 is an enlarged detail of FIG. 6 showing the intermeshing of the bottom and top layers respectively of the upper and lower dental crown seating wafers.

The dental crown seating wafer of this invention is generally indicated at 12 in FIGS. 1, 3, 4, 5, 6, 7, 8, 9, 10 and 11. The dental crown seating wafer has central solid core 14 as its major structural element. The central core 14 has a substantially rectangular outline and is in the form of a fairly thin injection molded part made of themoplastic synthetic polymer composition material. The polymer composition material should be moderately rigid, but should be sufficiently resilient that the material will yield slightly on impact. Such composition can be obtained for example from DuPont "Elvax" 660 resin which is a copolymer of ethylene and vinyl acetate containing 12% vinyl acetate. The core is seen from the front in FIG. 1, from the side in FIG. 3, and from the back in FIG. 5. Core 14 is limited by top edge 16, left and right edges 18 and 20, and bottom edge 22. These edges are preferably straight, but need not be, and may be decoratively configured. Central core 14 is molded as a substantially flat structure 0.060 inches (1.5 mm) thick, continuous on the back, but with a raised platform molded into the front surface from step 24 to top edge 16 to constitute free bite area 26 which is 0.095 inches (2.4 mm) in thickness from front to back surface. Near the top of free bite area 26, and essentially equidistant from left and right edges 18 and 20 is circular opening 28 which completely penetrates free bite area 26 from front to back. On the front surface of central solid core 14, from step 24 to left and right edges 18 and 20, and bottom edge 22, is border area 30, which is substantially flat, and is part of central core 14, and of the same thickness. A similar but wider border area 32 is located circumferentially on the back surface of central solid core area 14, and continues horizontally to form the back surface of the free-bite area 26. Within the circumscribed area formed by front and back border areas 30 and 32 central core 14 is molded into a multiplicity of small raised hemispheres, so formed that the circular base of each hemisphere is merged with the base of each abutting hemisphere, constricting the circular bases into a contiguous, thicker, inter-related lattice-like structure surrounding common internal open areas of core 14, and ending as semi-circular bases only in those areas that comprise the borders. The hemispheres are 0.0325 inches in height, and on the non-abutting base areas are 0.0325 inches in diameter. The combined thickness of front hemispheres, central core, and back hemispheres is a maximum of 0.125 inches (3 mm) uncompressed, while the inter-hemisphere open areas and border areas are central core thickness of 0.060 inches. FIG. 10 shows the effect of firm biting pressure on the layers of hemispheres. Under sustained biting pressures, the cusps of the teeth in opposing arches compress some hemispheres, and penetrate the central core slightly in the open areas, to result in a compressed bite-resisting layer of firm polymer material 34 of approximately 0.065 inches (1½ mm), separating crown 36 and opposing teeth 38 and 40 by this amount, and comprising a solid, very slightly resilient bite plane. FIG. 11 is an isometric view of the embodiment of the crown-seating wafer with additional vertical walls 42, 44, 46, and 48 which support cotton rolls 50 to aid in keeping the field surrounding the artificial crown 36 dry.

The most convenient method of use for this invention is for the dentist to place the artificial crown over the tooth stump, place the flat free-bite area 26 between the crown and the opposing teeth, and have the patient bite down gently and then firmly to seat the crown entirely onto the stump. Following the customary procedures for verifying crown fit, appearance, and function, the crown is removed. The customary procedures are followed to prepare the stump and crown for cementation. The crown, with dental cement layer placed within, is replaced over the stump, and the patient again seats it on the stump by biting down very firmly against free-bite area 26. Once the dentist feels the crown is suitably firmly seated, he employs the customary methods to force it still further into final cementation position. The raised hemisphere end of the wafer is then placed between the crown and the opposing teeth by the dentist holding the free-bite area 26 and using it as a handle to easily manipulate the wafer. A second wafer is placed on the opposite side of the mouth from that of the artificial crown to balance biting pressure on the musculature and jaw condyles. If a bridge that is wider than the width of the wafer is being placed, multiple wafers may be used to assure even distribution of pressure against the bridge components by the opposing teeth. Only one wafer opposite the most posteriorly-placed bridge-cementing wafers is necessary to balance the bite-pressures on the opposite side. Opening 28 may be used if desired to place a loop of dental floss 52 to be draped outside of the mouth of a comatose or otherwise physically handicapped patient for preventing inadvertant ingestion of the wafer, or for its retrieval in that event. The patient is then directed to bite as firmly as is comfortably possible egainst the wafer, and to continue the same firm biting pressure until told to relax. If significant muscle discomfort is experienced from tiring, patient may relax momentarily, and resume bite pressure duplicating as closely as possible the previous conditions, and maintaining them as long as possible. At the expiration of the setting time of the dental cement, the wafers are removed and discarded.

Another form of the embodiment is that in which there is incorporated means for keeping dry the field of operation. In the more preferable embodiment (FIG. 11), this may include supporting cotton rolls. In this form, dry cotton rolls are placed between vertical walls 42, 44, 46, 48 of the wafer which support them, and the wafer is placed between the appliance and the opposite teeth. The outlined procedure is then followed. The cotton rolls (50) are conveniently held where they will help to maintain field dryness, and will not interfere with the cementation procedure.

If an appliance is being placed that is insufficient in height to reach the approximate plane of occlusion of the neighboring teeth, two or more wafers may be placed together, one above the other, in the same orientation, with the lower surface of the upper one against the upper surface of the lower one. The protuberances will intermesh to form a stable platform under firm biting pressures that is twice the thickness of a single wafer. In this manner the upper lateral incisor, which is usually ½ to 1 millimeter short of the plane of its proximal teeth, may be successfully cemented. It is helpful to cut the upper wafer longitudinally to ½ its width to accomodate the narrower width of the upper lateral incisor, and employ this narrower wafer strip above the full-sized lower one for cementing these teeth.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A dental crown seating wafer for mediating inter-jaw biting pressure, comprising:

wafer means for positioning between the teeth of opposing arches, said wafer means generally defining a plane for the transfer of biting pressure between arches;

said wafer means having an upper and a lower surface, each of said surfaces having a plurality of outwardly extending non-rupturable protrusions, said protrusions forming respective upper and lower discontinuous resilient surfaces for resilient engagement by tooth areas impinging against said upper and lower discontinuous resilient surfaces, said resilient protrusions having sufficient structural strength to prevent their destruction under strong biting pressure from such impinging tooth areas.

2. The dental crown seating wafer of claim 1 wherein said wafer means comprises a substantially planar solid central core of resilient thermoplastic polymer material;

at least one section of said central core containing said upper and lower discontinuous resilient surfaces of similar material, said outwardly-extending protrusions from said upper and lower surfaces constructed so that the bases of said protrusions extend outward from said solid central core, said bases partially intermesh with each abutting base, and the outermost surfaces of said protrusions may be spaced apart, so that under strong biting pressure said outermost protrusion areas are compressed toward their bases, said bases become spread and said spaces are progressively lessened so that said upper and lower multitudes of resilient protrusions become compacted and form a progressively thinner, denser, and less resilient layer pregressively more resistant to biting pressure, until the effective resilience of the central core material is reached with strong biting pressures, and minimal thickness is attained.

3. The dental crown seating wafer of claim 2 wherein said central core and said resilient protrusions comprise maximum uncompressed thickness equal to or greater than the average resting space between the upper and lower teeth when the muscles of mastication are at rest, and wherein the resilience of said uncompressed wafer is greatest; and wherein under said strong biting pressure said compacted protrusions and said core comprise minimum compressed thickness equal to at least the minimum average resting space between the upper and lower teeth when the muscles of mastication are at rest, and wherein the resilience of said wafer is least.

4. The dental crown seating wafer of claim 2 wherein said central core and said protrusions are unitarily formed as a single part of injection-molded thermoplastic synthetic polymer composition material.

5. The dental crown seating wafer of claim 2 wherein said central core has a flattened end free of protrusions, said flattened end having a thickness equal to the remainder of said wafer including protrusions.

6. The dental crown seating wafer of claim 2 wherein said flattened end of said central core includes a small opening penetrating therethrough for receiving a loop of dental floss for safety and retrieval purposes.

7. The dental crown seating wafer of claim 2 wherein said upper and lower discontinuous resilient layers are arranged in spatially meshing relationship with each other so that, when one such wafer is placed on top of a second such wafer, said lower layer of protrusions of one wafer will intermesh with said upper layer of protrusions of such second wafer to form a stable, multiple-layered series of wafers.

8. The dental crown seating wafer of claim 2 wherein sid central core and said uncompressed upper and lower protrusion-containing layers of said wafer is of maximum thickness of approximately 3 mm. and is of maximum resilience and minimally resistant to biting pressure.

9. The dental crown seating wafer of claim 2 wherein the minimum thickness when compressed of said protrusion-containing layers and said core of said wafer is 1 mm., said compressed wafer is maximally compacted, and is of the approximate resilience of said thermoplastic polymer material, and optimally transfers biting pressure between the arches.

* * * * *